United States Patent
Wei et al.

[11] Patent Number: 5,570,710
[45] Date of Patent: Nov. 5, 1996

[54] DENTAL FLOSS HOLDER

[76] Inventors: Kuang-Hsing Wei; Kuang-Hung Wei, both of 18500 Bay Leaf Way, Germantown, Md. 20874

[21] Appl. No.: 528,889

[22] Filed: Sep. 15, 1995

[51] Int. Cl.$^6$ .................................................. A61C 15/00
[52] U.S. Cl. ...................... 132/323; 132/321; 132/324; 132/328; 132/329
[58] Field of Search ................................ 132/321, 323, 132/324, 326, 327, 328, 329

[56] References Cited

U.S. PATENT DOCUMENTS

| | | | |
|---|---|---|---|
| 2,644,469 | 7/1953 | Cohen | 132/324 |
| 3,949,769 | 4/1976 | Minka | 132/323 |
| 4,050,470 | 7/1977 | Miller | 132/323 |
| 4,403,625 | 9/1983 | Sanders et al. | 132/323 |
| 5,199,452 | 4/1993 | Cheng | 132/323 |
| 5,503,168 | 4/1996 | Wang | 132/323 |

*Primary Examiner*—Gene Mancene
*Assistant Examiner*—Pedro Philogene

[57] ABSTRACT

A reusable dental floss holder to fasten securely a length of floss at its ends in lieu of winding ends of the length of floss around fingers for removing food particles and plaque from teeth surfaces has cover and base members engaging with each other to fasten the floss to be manipulated easily by hands in mouth.

17 Claims, 3 Drawing Sheets

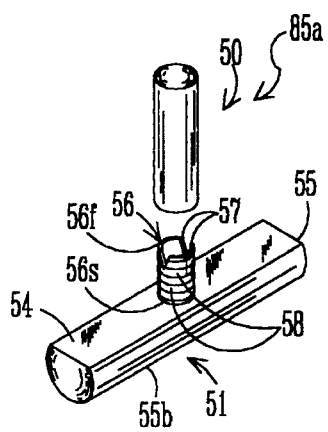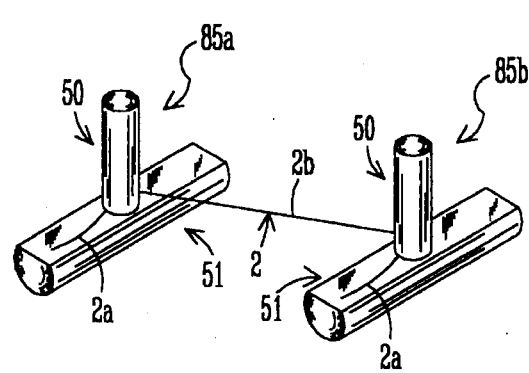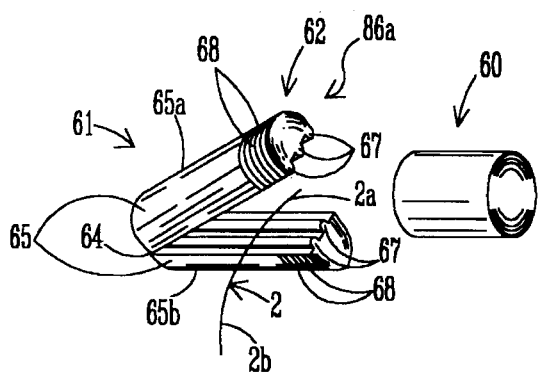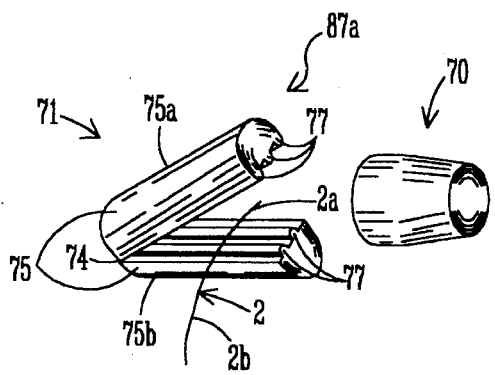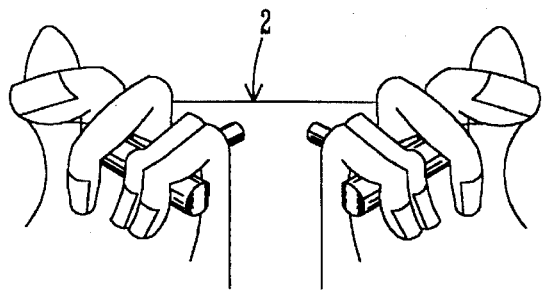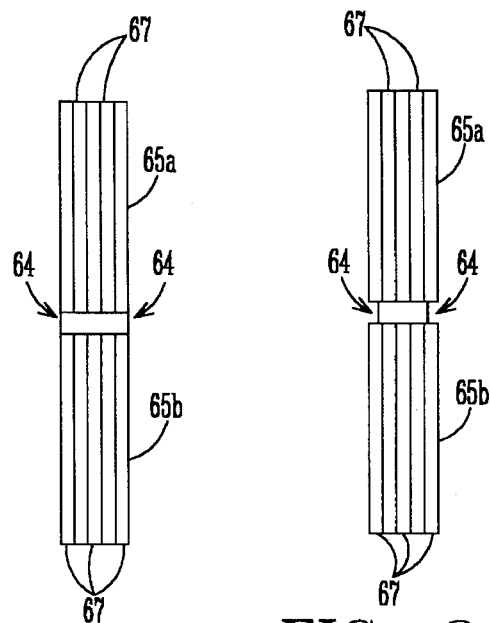
FIG. 15. FIG. 16. FIG. 18. FIG. 19. FIG. 17. FIG. 20. FIG. 21.

DENTAL FLOSS HOLDER

FIELD OF INVENTION

This invention relates to the cleaning of teeth with a length of dental floss and provides as its general object an improved device which can be used to fasten dental floss easier and to render teeth-cleaning more effectively.

SUMMARY OF THE INVENTION

There are many devices attempting to render flossing less tedious and make it more effective and convenient. Moreover, a growing number of dentists and orthodontists recommend highly for cleaning teeth daily by using dental floss to remove food particles between teeth. However, most people still don't floss daily, even those who take teeth-cleaning and dental care seriously. The inconvenience and discomfort for maneuvering the dental floss by winding ends of a length of floss around two fingers is the main reason. The winding ends of a length of floss around two fingers will not only cause discomfort on fingers but also render difficulties in manipulating in mouth. Although there are numerous devices with a predetermined length of floss fixed in a two-pronged dental device, maneuvering with two fingers winding a length of dental floss is still the most effective way of daily dental floss cleaning, especially for reaching and positioning between the rear most teeth, and is highly recommended by the dental profession. U.S. Pat. 4,050,470 to Miller (1977) provides a dental floss holder with an inwardly tapered slot extending along one elongate edge which does not fasten the dental floss securely in place to facilitate the manipulating of the floss in mouth. Accordingly, several objects and advantages of the present invention are:

(a) to provide an improved dental floss holder which is used to eliminate the discomfort caused by winding a length of floss around fingers;

(b) to provide an improved dental floss holder which is designed to save the wasteful of floss for winding an extra length of floss around fingers;

(c) to provide an improved dental floss holder to facilitate securely fixed floss ends than winding around fingers which is needed to be rewound several times during the course of teeth-cleaning; and (d) to provide an improved dental floss holder to better control of a strained floss and perform a more effective teeth-cleaning.

Further objects and advantages of the invention will become apparent from the appended drawings and the ensuing specifications.

DRAWING FIGURES

FIG. 15 is a perspective view of a fifth embodiment of a floss holder;

FIG. 16 is a perspective view of the holder in FIG. 15 connecting in a pair with a dental floss;

FIG. 17 is a perspective view shown the use of the fifth embodiment of the floss holder;

FIG. 18 is a perspective view of a sixth embodiment of a floss holder;

FIG. 19 is a perspective view of a seventh embodiment of a floss holder;

FIG. 20 is a front view of the embodiment in FIG. 18 showing a springable base member fully opened; and FIG. 21 is a front view of the embodiment in FIG. 18 showing a hinged base member fully opened.

DETAILED DESCRIPTION OF THE PREFERRED EMBODIMENT

Figure 1:
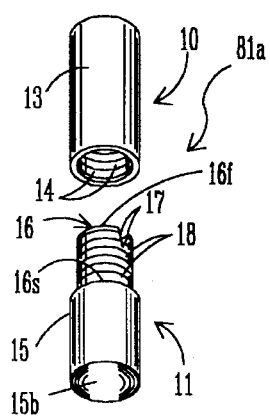
FIG. 1 is a perspective view of the new floss holder.
Figure 1A:
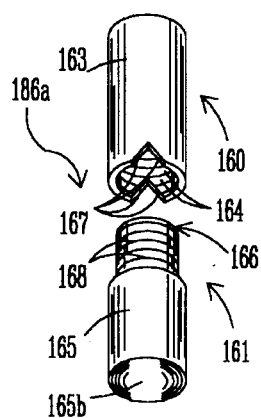
FIG. 1a is a perspective view of an alternative embodiment in FIG. 1 with a notch created at different place.
Figure 2:
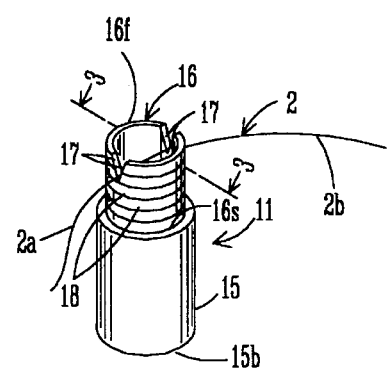
FIG. 2 is a perspective view of the base member of FIG. 1 with a floss.
Figure 3:
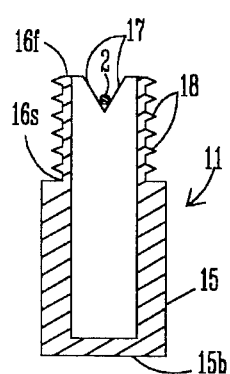
FIG. 3 is a sectional elevation of the base member in position taken on the line 3—3 of FIG. 2.
Figure 4:
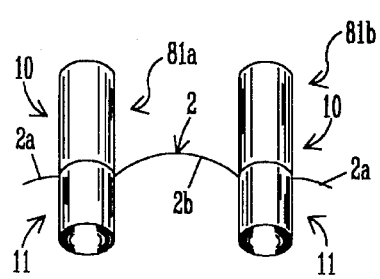
FIG. 4 is a perspective view of the floss holder in FIG. 1 connecting in a pair with a dental floss.
Figure 13:
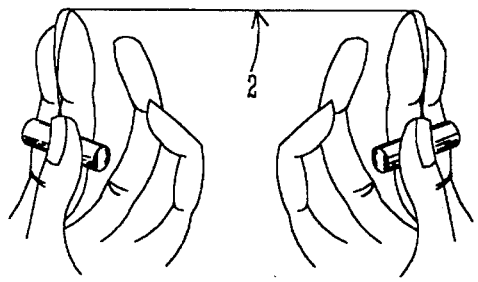
FIG. 13 is a perspective view shown the use of the floss holders with both hands.
Figure 14:
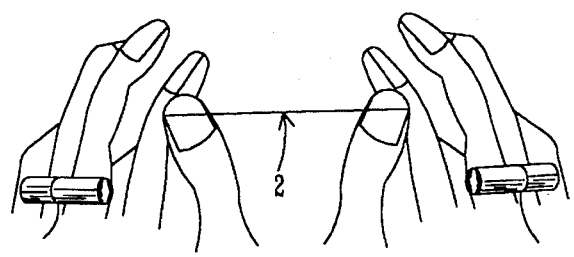
FIG. 14 is a perspective view shown another way of use of the floss holders with both hands.

A first of various preferred embodiments of the dental floss holder of the present invention is shown in FIGS. 1–4 and the methods of operating the device are illustrated in FIGS. 13–14. In FIG. 1, a first dental floss holder 81a comprises a cover member 10 and a base member 11. Cover member 10 includes a screw cap 13 and internal screw threads 14. Base member 11 includes a screw base 15 and a screw head 16. Screw base 15 includes a screw base bottom 15b. Screw head 16 comprises a notch 17 and external screw threads 18. Screw head 16 also includes a first end 16f and a second end 16s. Second end 16s of screw head 16 is connected to screw base 15. FIG. 2 illustrates base member 11 with a dental floss 2, having floss ends 2a and 2b, inserted in notch 17. FIG. 3 is a sectional view of base member 11 in position taken on the line 3—3 of FIG. 2. Referring to FIG. 4, it shows a pair of dental floss holders working together wherein cover member 10 is screwed together with base member 11 having dental floss 2 fastened securely connecting dental floss holder 81a and a second dental floss holder 81b. Dental floss holders 81a and 81b are identical. Notch 17 is an angular cut on first end 16f of screw head 16 to facilitate easy insertion of dental floss 2 onto screw head 16. The depth of notch 17 is about one-third the height of screw head 16. When dental floss 2 is placed inside notch 17, the length of floss end 2a is shorter than that of floss end 2b which extends to the second dental floss holder 81b, shown in FIG. 4. Floss end 2b is the portion where the tension is applied to insert dental floss 2 in between teeth for cleaning, whereas floss end 2a, requiring no load, is the free end which extends out from notch 17 to reach down approximately to screw base bottom 15b. When cover member 10 screws together with base member 11 with dental floss 2 in notch 17, floss ends 2a and 2b are fastened tightly in between internal screw threads 14 and external screw threads 18. Referring to FIG. 13, it illustrates right hand and left hand grasp dental floss holders 81a and 81b in their palms, and the middle fingers hold against floss end 2b to apply tension thereon by moving each hand away from each other to form a straight-line of floss end 2b. The strained floss end 2b is ready to be manipulated between teeth in mouth. The present invention eliminates the discomfort caused by winding a length of floss around fingers, saves the wasteful of floss for winding extra length around fingers, facilitates securely fixed floss ends than winding around fingers which is needed to be rewound several times during the course of teeth-cleaning, provides a better control of a strained floss, and performs a more effective teeth-cleaning. Referring to FIG. 14, it illustrates another method of manipulating dental floss holders 81a and 81b. Dental floss holders 81a and 81b are held against the back of hands, and then the thumb and index finger hold floss end 2b to apply tension thereon by moving both hands away from each other to form a straight-line of floss end 2b. Referring now to FIG. 1a, it shows an alternative embodiment of dental floss holder 81a of the present invention. A first dental floss holder 186a comprises a cover member 160 and a base member 161. Cover member 160 includes a screw cap 163 comprising internal screw threads 164 and a notch 167. Base member 161 includes a screw base 165 comprising a screw base bottom 165a and a screw head 166 which includes external screw threads 168. Dental floss holders 81a and 186a show that notch 167 can be created on either cover or base members.

Figure 5:
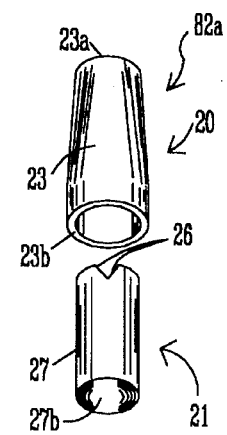
FIG. 5 is a perspective view of another embodiment of a floss holder.
Figure 6:
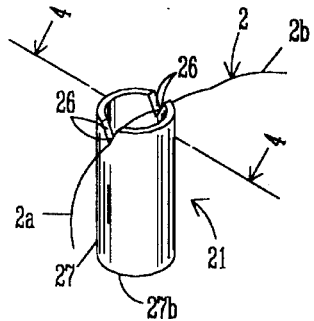
FIG. 6 is a perspective view of the base member of FIG. 5 with a floss.
Figure 7:
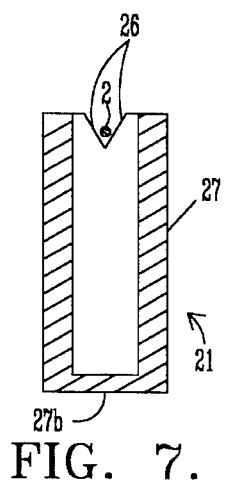
FIG. 7 is a sectional elevation of the base member in position taken on the line 4—4 of FIG. 6.
Figure 8:
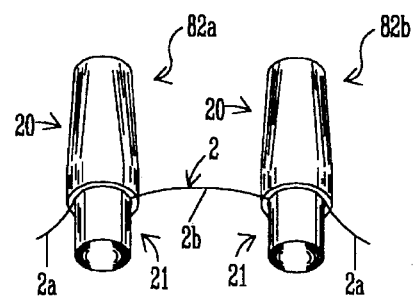
FIG. 8 is a perspective view of the floss handler in FIG. 5 connecting in a pair with a dental floss.

FIGS. 5–8 show another embodiment of the dental floss holder of the present invention and FIGS. 13–14 illustrate the methods of operating the holder. In FIG. 5, a first dental floss holder 82a comprises a cover member 20 and a base member 21. Cover member 20 includes a peg cover 23 comprising a cover top 23a and a cover bottom 23b. Base member 21 includes a peg 27 comprising a notch 26 and a peg bottom 27b. The inner diameter of cover top 23a is slightly smaller than that of cover bottom 23b to form a conical-like shape of cover member 20. Base member 21 is of a cylindrical shape whose outer diameter is slightly smaller than the inner diameter of cover bottom 23b but slightly greater than the inner diameter of cover top 23a. When cover member 20 is pushed down to cover up base member 21, the difference in diameters allow cover member 20 to cover up base member 21 securely, especially with dental floss 2 in between. FIG. 6 illustrates base member 21 with dental floss 2 inserted onto notch 26. FIG. 7 is a sectional view of base member 21 in position taken on the line 4–4 of FIG. 6. Referring to FIG. 8, it shows dental floss holder 82a working together with a second dental floss holder 82b, identical to dental floss holder 82a, in a pair wherein base members 21 is covered securely together by cover members 20 with dental floss 2 fastened in position connecting both holders. Notch 26 is an angular cut on the top of peg 27 to facilitate the insertion of dental floss 2 onto peg 27. The depth of notch 26 is about one-sixth the height of peg 27. When dental floss 2 is placed inside notch 26, the length of floss end 2a is shorter than that of floss end 2b which extends to second dental floss holder 82b as shown in FIG. 8. Floss end 2b is the portion where the tension is applied to insert dental floss 2 in between teeth for cleaning, whereas floss end 2a, requiring no load, is the free end which extends out from notch 26 to reach down approximately to peg bottom 27b. When cover member 20 is pushed down to cover base member 21 with dental floss 2 inside notch 26, floss ends 2a and 2b are squeezed tightly in between peg 27 and the conical-like peg cover 23. The preferred material for cover member 20 is plastic with rigid property but can be expanded outward slightly when cover member 20 engages with base member 21. The operations of dental floss holders 82a and 82b in FIGS. 13–14 are the same as they do for dental floss holders 81a and 81b. It is obvious that dental floss holders 81a, 81b, 82a, 82b, and 186a can be paired in any combinations to clean teeth.

Figure 9:
FIG. 9 is a perspective view of a third embodiment of a floss holder.
Figure 9A:
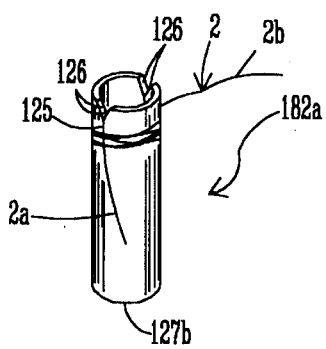
FIG. 9a is a perspective view of an alternative embodiment of a floss holder in FIG. 9.
Figure 10:
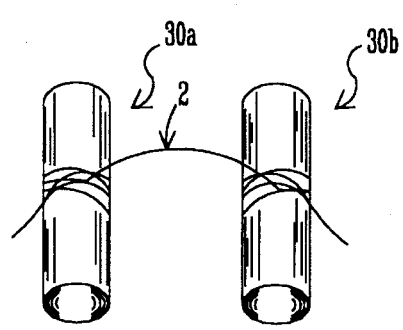
FIG. 10 is a perspective view of the holder in FIG. 9 connecting in a pair with a dental floss.
Figure 10A:
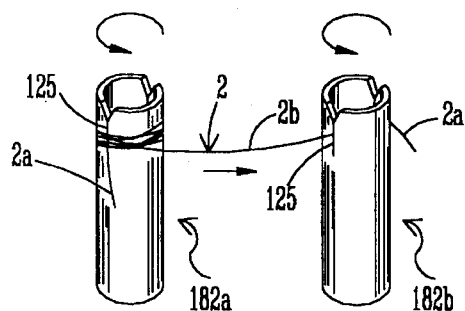
FIG. 10a is a perspective view of the holder in FIG. 9a connecting in a pair with a dental floss, both holders rotating counterclockwise to wind and unwind the floss.
Figure 11:
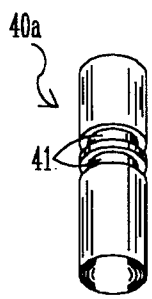
FIG. 11 is a perspective view of a fourth embodiment of a floss holder.
Figure 12:
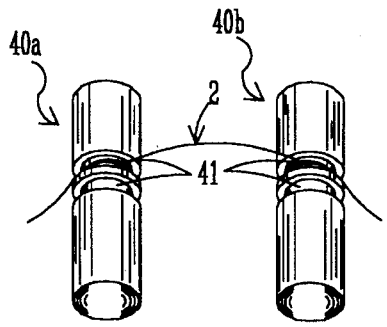
FIG. 12 is a perspective view of the holder in FIG. 11 connecting in a pair with a dental floss.

FIGS. 9–12 show a third and fourth embodiments of the dental floss holder of the present invention and FIGS. 13–14 illustrate the methods of operating the holders. In FIG. 9, a first dental floss holder 30a is an one-piece elongate bar having preferred shape of circular cylinder. FIG. 10 shows dental floss 2 is winding around dental floss holder 30a and a second dental floss holder 30b, identical to dental floss holder 30a, to fasten dental floss 2 so that dental floss holders 30a and 30b can be manipulated like dental floss holders 81a and 81b in FIGS. 13–14. In FIG. 9a, it presents an alternative embodiment of dental floss holder 30a. A first dental floss holder 182a is also an one-piece elongate holder comprising a notch 126, a gap 125 and a holder bottom 127b. Floss end 2a is inserted into notch 126 and pulled down into gap 125 to reach down approximately to holder bottom 127b to be securely held in gap 125, and then floss end 2b is winding around dental floss holder 182a to further secure dental floss 2. In FIG. 10a, floss end 2b reaches to a second dental floss holder 182b, identical to dental floss holder 182a. The winding of floss end 2b around holders serves two purposes: one is to fasten dental floss 2 securely on the holder; another is to store an extra length of dental floss 2 by winding on the holder so that floss end 2b can be easily unwound and rewound to use different sections of floss end 2b. As shown in FIG. 10a, dental floss holders 182a and 182b are paired together to rewind and unwind floss end 2b. Dental floss holders 182a and 182b rotate counterclockwise to unwind floss on dental floss holder 182a and rewind floss on dental floss holder 182b. Floss end 2b moves from dental floss holder 182a to 182b. These will allow floss users, who like to clean their teeth with clean, new sections of dental floss for every tooth, to change sections of floss end 2b easier. Still in FIG. 11, a dental floss holder 40a comprising grooves 41 is also an one-piece elongate bar having preferred shape of circular cylinder. FIG. 12 shows dental floss 2 is winding around grooves 41 to fasten dental floss 2 in place so that dental floss holder 40a and a second dental floss holder 40b, identical to dental floss holder 40a, can be used like dental floss holders 182a and 182b.

FIGS. 15–16 show a fifth embodiment of the dental floss holder of the present invention and FIG. 17 presents the method of manipulating the holder. In FIG. 15, a dental floss holder 85a comprises a cover member 50, identical to cover member 10, and a base member 51. Base member 51 includes a screw base 55 having a base platform 54 and a base bottom 55b, and a screw head 56 having a notch 57 and external screw threads 58. Screw head 56 also includes a first end 56f and a second end 56s. Second end 56s of screw head 56 is connected to base platform 54 of base member 51. Base platform 54 is a flat platform designed to facilitate the fastening of dental floss 2 inside notch 57. When dental floss 2 is inside notch 57, floss end 2a rested on base platform 54, as seen in FIG. 16, can be pressed and held by a finger while screwing down cover member 50 to fasten securely dental floss 2. In FIG. 16, it shows dental floss holder 85a and a second dental floss holder 85b, identical to dental floss holder 85a, working together wherein cover members 50 are screwed together with base members 51 with dental floss 2 fastened in position connecting both holders. Referring to FIG. 17, it illustrates right hand and left hand grasp dental floss holders 85a and 85b in their palms with cover members 50 sticking out between the middle and ring fingers to add an extra grip. The thumbs and index fingers hold floss end 2b to apply tension thereon by moving each hand away from each other to form a straight-line of floss end 2b.

Referring now to FIGS. 18–21, a sixth and seventh embodiments of the dental floss holder of the present invention and FIGS. 13–14 illustrate the methods of operating the holders. In FIG. 18, a first dental floss holder 86a comprises a cover member 60, identical to cover member 10, and a base member 61. Base member 61 includes a screw head 65 having a first leg 65a and a second leg 65b, both legs having projections 67 and external screw threads 68. Projections 67 are added to facilitate the fastening of dental floss 2. A connecting means 64 connects first and second legs 65a and 65b. FIGS. 20–21 show base members 61 with first leg 65a and second leg 65b opening up fully. In FIG. 20, it shows connecting means 64 is a springable connection and in FIG. 21 a hinged connection. Dental floss 2 is placed on second leg 65b with floss ends 2a and 2b on either side. When first leg 65a and second leg 65b engage with each other, dental floss 2 is securely held in between projections 67. When both legs closed together with dental floss 2 in between, cover member 60 screws in with base member 61 to securely fasten dental floss 2 to be used like dental floss holder 81a. In FIG. 19, a dental floss holder 87a includes a cover member 70, identical to cover member 20, and a base member 71. Base member 71 includes a peg 75 having a first leg 75a and a second leg 75b, both legs having projections 77. A connecting means 74 connects first and second legs 75a and 75b. Connecting means 74 is equivalent to connecting means 64. The operations of dental floss holder 87a is similar to dental flosss 86a and 82a.

Although the description above contains many specifications, these should not be construed as limiting the scope of the invention but as merely providing illustrations of some of the presently preferred embodiments of this invention. For example, the shape of screw base 15 can be circular cylinder or rectangular box or pentagon box. The preferred material for the dental floss holder is plastic; however, metal can be another choice. Thus the scope of the invention should be determined by the appended claims and their legal equivalents, rather than by the examples given.

What is claimed is:

1. A dental floss holder for securely fastening one end of a dental floss, said holder comprising:
   (a) a cover member having screw threads thereon;
   (b) a screw head having a first end and a second end, said screw head having matching screw threads thereon so that when said cover member screws together with said screw head, the floss is fastened between said screw threads of said cover member and said screw head; and
   (c) a screw base connected to said second end of said screw head, said screw base being an elongated configuration adapted to be handled by fingers, whereby when the floss is placed across said first end of said screw head, the floss may be held by fingers against said screw base so as to facilitate the screwing together of said screw threads, whereby when the floss is securely fastened between said screw threads, said holder having the floss fastened therein is manipulated by a hand in lieu of winding the floss around a finger for teeth cleaning.

2. The holder of claim 1, wherein said screw head further comprises:
   (a) a notch defining a substantially V-shaped angular cut, said notch being formed substantially on said first end of said screw head to facilitate the fastening of the floss, whereby when the floss is held against said screw base, the floss is also across inside said notch so that the floss is ready to be fastened between said screw threads.

3. The holder of claim 2, wherein:
   (a) said screw threads of said cover member are internal screw threads; and
   (b) said matching screw threads of said screw head are external screw threads.

4. The holder of claim 3, wherein:
   (a) the longitudinal length of said notch is about one-third that of said screw head.

5. The holder of claim 1, wherein:
   (a) said screw threads of said cover member are internal screw threads; and
   (b) said matching screw threads of said screw head are external screw threads.

6. A dental floss holder for securely fastening one end of a dental floss, said holder comprising:
   (a) a cover member having screw threads thereon; and
   (b) a base member being a configuration adapted to be handled by fingers, said base member having matching screw threads thereon so that when said cover and base members are threadably engaging with each other, the floss is securely fastened between said screw threads of said cover and base members, whereby when the floss is securely fastened between said screw threads, said holder having the floss fastened therein is manipulated by a hand in lieu of winding the floss around a finger for teeth cleaning.

7. The holder of claim 6, wherein said base member further comprises:
   (a) a notch defining an angular cut formed substantially on one end of said screw threads of said base member to facilitate the fastening of the floss, whereby when the floss is placed inside said notch and extends out to two sides of said base member, the floss may be held against both sides of said base member to facilitate the fastening of the floss.

8. The holder of claim 7, wherein:
   (a) said screw threads of said cover member are internal screw threads; and
   (b) said matching screw threads of said base member are external screw threads.

9. The holder of claim 8, wherein:
   (a) the longitudinal length of said notch is about one-third that of said screw threads of said base member.

10. The holder of claim 6, wherein:
    (a) said screw threads of said cover member are internal screw threads; and
    (b) said matching screw threads of said base member are external screw threads.

11. A dental floss holder for securely fastening one end of a dental floss, said holder comprising:

(a) a cover member having internal screw threads thereon;

(b) a screw head having a first end and a second end, said screw head having matching external screw threads thereon so that when said cover member screws together with said screw head, the floss is securely fastened between said internal and external screw threads;

(c) a screw base connected to said second end of said screw head, said screw base being an elongated configuration adapted to be handled by fingers, whereby when the floss is placed across said first end of said screw head, the floss may be held by fingers against said screw base to facilitate the screwing together of said screw threads; and (d) said screw head having a notch defining a substantially V-shaped angular cut, said notch being formed substantially on said first end of said screw head to facilitate the fastening of the floss, whereby when the floss is held against said screw base, the floss is also across inside said notch so that the floss is ready to be fastened between said screw threads, whereby when the floss is securely fastened between said screw threads, said holder having the floss fastened therein is manipulated by a hand in lieu of winding the floss around a finger for teeth cleaning.

12. The holder of claim 11, wherein:

(a) the longitudinal length of said notch is about one-third that of said screw head.

13. A method of securely fastening one end of a dental floss, comprising the steps of:

(a) placing the floss on a base member having screw threads thereon; and (b) screwing a cover member having matching screw threads thereon with said screw threads of said base member so that when said cover member screws together with said base member, the floss is securely fastened between said screw threads, whereby said cover and base members having the floss securely fastened therein are manipulated by a hand in lieu of winding the floss around a finger for teeth cleaning.

14. The method of claim 13, wherein the placing step further comprises the step of:

(a) inserting the floss across inside a notch to facilitate the fastening of the floss, whereby when the floss is placed on said base member and across inside said notch, the floss is ready to be fastened between said screw threads.

15. The method of claim 14, wherein the screwing step is performed by screwing together internal screw threads of said cover member with external screw threads of said base member.

16. The method of claim 15, wherein the inserting step is performed by placing the floss into said notch a longitudinal length about one-third that of said screw threads of said base member.

17. The method of claim 13, wherein the screwing step is performed by screwing together internal screw threads of said cover member with external screw threads of said base member.

* * * * *